United States Patent [19]

Baylis

[11] 4,331,591

[45] May 25, 1982

[54] CHEMICAL PROCESS FOR THE PRODUCTION OF α-AMINOPHOSPHONIC ACIDS AND PEPTIDE DERIVATIVES

[75] Inventor: Eric K. Baylis, Stockport, England

[73] Assignee: Ciba-Geigy Corporation, Ardsley, N.Y.

[21] Appl. No.: 80,763

[22] Filed: Oct. 1, 1979

[30] Foreign Application Priority Data

Oct. 5, 1978 [GB] United Kingdom ............... 39399/78

[51] Int. Cl.³ ...................... C07C 103/52; C07C 9/02; C07G 7/00
[52] U.S. Cl. ........................... 260/112.5 R; 260/502.5; 260/970; 260/985
[58] Field of Search .................... 260/112.5 R, 502.5, 260/970, 985

[56] References Cited

U.S. PATENT DOCUMENTS

| | | | |
|---|---|---|---|
| 2,899,455 | 8/1959 | McBee et al. | 260/451 |
| 2,952,699 | 9/1960 | Norman | 260/985 |
| 3,187,035 | 6/1965 | Schrader et al. | 260/985 |
| 3,277,217 | 10/1966 | Nehmsmann et al. | 260/985 |
| 3,333,030 | 7/1967 | Baranauckas et al. | 260/985 |
| 4,016,148 | 4/1977 | Atherton et al. | 260/112.5 R |
| 4,028,403 | 6/1977 | Sanderson | 260/502 |

FOREIGN PATENT DOCUMENTS 2721761 5/1977 Fed. Rep. of Germany.

OTHER PUBLICATIONS

Kosolapoff, G., Organophosphorus Compounds, p. 137, New York, John Wiley and Sons, Inc.
Kosolapoff and Maier, Organic Phosphorus Compounds, New York, John Wiley and Sons.
Hickinbottom, W., Reaction of Organic Compounds, John Wiley and Sons, Inc., N.Y. 3rd Ed., pp. 420–432 (1962).

*Primary Examiner*—Blondel Hazel
*Attorney, Agent, or Firm*—Michael W. Glynn

[57] ABSTRACT

The present invention provides a process for the production of physiologically-useful α-aminophosphonic acids and peptide derivatives of the formula:

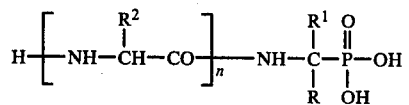

wherein

R and $R_1$ may be the same or different and each can be hydrogen, deuterium or an optionally substituted lower alkyl group, lower alkenyl, lower alkynyl, cycloalkyl, aryl or heterocyclic radical containing one or more oxygen, nitrogen or sulphur atoms and which may be fused to an aromatic ring, a lower alkyl group substituted by a cycloalkyl radical, a lower alkyl group substituted by an aryl radical, a lower alkyl group substituted by a heterocyclic radical as defined above or R and $R_1$ together form a polymethylene chain optionally interrupted by an oxygen, nitrogen or sulphur atom, or $R_1$ represents, together with the C(R)—N< residue to which it is attached, the atoms required to complete a heterocyclic radical; and $R_2$ can be hydrogen, optionally substituted lower alkyl, cycloalkyl, aryl or lower alkyl substituted by a cycloalkyl radical, lower alkyl substituted by a heterocyclic radical containing one or more nitrogen atoms; by a heterocyclic radical containing one or more nitrogen atoms, or $R_2$ together with the C(H)—N residue to which it is attached, may represent the atoms required to complete a heterocyclic radical; and n is 0, 1, 2, 3 or 4; comprising oxidizing, using an oxidizing agent, a compound having the formula:

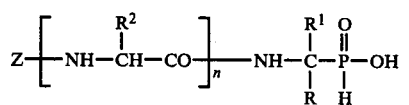

wherein

R, $R^1$, $R^2$ and n have their previous significance, and Z is H or a protecting group usually used for an amino group; and then removing any protecting group.

12 Claims, No Drawings

CHEMICAL PROCESS FOR THE PRODUCTION OF α-AMINOPHOSPHONIC ACIDS AND PEPTIDE DERIVATIVES

The present invention relates to a new chemical process, especially to a new process for the production of α-amino phosphonic acids and their peptide derivatives.

In our copending British Patent Applications Nos. 21000/76 and 482641/77 there are described certain α-aminophosphonous acids and their peptide derivatives.

We have now found, surprisingly, that these compounds can be oxidised to the corresponding phosphonic acids or derivatives, without affecting the amino groups.

Accordingly, the present invention provides a process of producing an α-aminophosphonic acid compound or a peptide derivative of the formula:

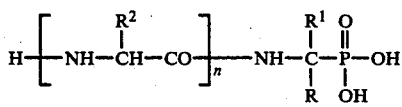

wherein
R and $R_1$ may be the same or different and each can be hydrogen, deuterium or an optionally substituted lower alkyl group, lower alkenyl, lower alkynyl, cycloalkyl, aryl or heterocyclic radical containing one or more oxygen, nitrogen or sulphur atoms and which may be fused to an aromatic ring, a lower alkyl group substituted by a cycloalkyl radical, a lower alkyl group substituted by an aryl radical, a lower alkyl group substituted by a heterocyclic radical as defined above or R and $R_1$ together form a polymethylene chain optionally interrupted by an oxygen, nitrogen or sulphur atom, or $R_1$ represents, together with the C(R)—N< residue to which it is attached, the atoms required to complete a heterocyclic radical; and $R_2$ can be hydrogen, optionally substituted lower alkyl, cycloalkyl, aryl or lower alkyl substituted by a cycloalkyl radical, lower alkyl substituted by a heterocyclic radical containing one or more nitrogen atoms; by a heterocyclic radical containing one or more nitrogen atoms, or $R_2$ together with the C(H)—N residue to which it is attached, may represent the atoms required to complete a heterocyclic radical; and n is 0, 1, 2, 3 or 4; comprising oxidising, using an oxidising agent, a compound having the formula:

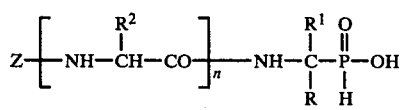

wherein
R, $R^1$, $R^2$ and n have their previous significance and Z is H or a protecting group, e.g. a benzyloxy carbonyl group, normally used for an amino acid; and removing any protecting group Z.

The reactant of formula II may be used as the free acid or as an ester thereof with a physiologically splittable alcohol; a salt of a compound of formula II, or their esters with a physiologically acceptable acid or base; including all optical isomers thereof. The α-amino acid residues or esters occurring in the peptides of formula I or II may have the D, L or L or D configuration.

The oxidation process of the present invention is carried out by contacting the α-amino phosphonous acid (or peptide derivative) of formula II with an oxidising agent.

Oxidising agents which may be used include salts of metals (capable of existing in higher and lower valency states) in their higher valency state in the presence of a hydroxylic solvent such as water; oxides of metals and non-metals capable of releasing oxygen; oxyacids (and their salts) of metals and non-metals, capable of releasing oxygen; organic compounds capable of releasing oxygen; halogens and halo-organic compounds in the presence of water; direct sources of oxygen; and peroxides.

Oxidising salts of metals capable of existing in higher or lower, including zero, valency states may include the salts of Group Ib, Group IIb, Group IIIb, Group IV, Group VIII and lanthanide elements, and are particularly, cupric salts such as cupric acetate, cupric carbonate, cupric chloride, and cupric sulphate; silver trifluoroacetate, auric chloride, mercuric chloride and mercuric acetate, thallic acetate, lead tetra acetate, ferric chloride, palladium acetate, and ceric ammonium nitrate.

Oxides of metals and non-metals may include the oxides of Group Ib, Group IIb, Group Vb, Group VIb, Group VIIa, Group VIIb and Group VIII elements and are particularly silver oxide, mercuric oxide, mercuric oxide/iodine, dinitrogen tetroxide, bismuth trioxide, sulphur dioxide, selenium dioxide, manganese dioxide, oxygen difluoride, and nickel peroxide.

Oxy acids of metals and non-metals may include the oxyacids of Group IIIb, Group Vb, Group VIa, Group VIb, Group VIIa, Group VIIb and Group VIII elements their salts, esters and halides, and are particularly salts of perboric acid such as sodium perborate; salts of bismuth oxyacids such as sodium bismuthate; salts of nitrous acid such as sodium nitrite; nitrosyl chloride; oxyacid derivatives of chromium such as chromic acid, sodium chromate, sodium dichromate, chromic anhydride, chromyl acetate, chromyl chloride, chromyl trichloracetate, and t-butyl chromate; Caro's acid; potassium peroxymonosulphate, sodium persulphate and potassium persulphate; salts of manganic and permanganic acid such as barium manganate, potassium manganate and potassium permanganate; salts and esters of oxyhaloacids such as sodium hypochlorite, potassium hypochlorite, sodium hypobromite, sodium bromate, sodium iodate, sodium periodate and sodium periodate/ruthenium tetroxide; potassium ferricyanide.

Organic compounds capable of releasing oxygen may include quinones, N-oxides, sulphoxides, and iodine oxides, and are particularly phenanthroquinones; pyridine N-oxide and N-methylmorpholine oxide; dimethyl sulphoxide; iodosobenzene and iodosobenzene diacetate.

Halogens, mixed halogens and halo-organic compounds may include chlorine, bromine, iodine, iodine pentafluoride, and N-halo compounds particularly N-bromoacetamide; bromocarbamide, N-bromosuccinimide, and N-chlorosuccinimide.

Direct sources of oxygen include oxygen, air, and ozone.

Peroxides may include hydrogen peroxide and organic peroxides such as peracetic acid, perbenzoic acid, m-chloroperbenzoic acid and pertrifluoroacetic acid.

In addition it is possible to effect the process of the invention by using enzymic, electrochemical and catalytic air oxidation techniques.

For reasons of process convenience and/or economics, preferred oxidising agents are mercuric chloride, cupric chloride, bromine/water, hydrogen peroxide, sulphur dioxide, silver oxide and sodium iodate.

The term "lower" referred to above and hereinafter in connection with organic radicals or compounds respectively, defines such with up to 6, preferably up to 3 carbon atoms.

The above listed radicals R, $R_1$ and $R_2$ optionally may be substituted by one or more functional groups, as for example, free or etherified hydroxy or mercapto groups, optionally converted carboxyl groups, S-substituted dithio groups, optionally substituted amino groups $-NR_3R_4-$ in which $R_3$ and $R_4$ may be the same or different and can be hydrogen or lower alkyl or optionally substituted guanidino and/or optionally substituted aryl groups or heterocyclic residues, or $R_3$ is a protecting group Z and $R_4$ is hydrogen.

Moreover R and $R_1$ as a lower alkyl group, aryl group or heterocyclic radical or an aryl group or heterocyclic radical as substituent of R or $R_1$ as lower alkyl group may be substituted by one or more halogen atoms, $-NR_3R_4$ groups in which $R_3$ and $R_4$ together form a polymethylene chain containing up to 6 carbon atoms which may optionally be interrupted by oxygen or nitrogen or an aryloxy group optionally substituted by hydroxy or an halogen atom as for example iodine.

The substituents R, $R_1$ and $R_2$ as lower alkyl group may be a straight or branched chain alkyl group of 1 to 6 carbon atoms and may be for example, methyl, ethyl, n-propyl, isopropyl, n-butyl, isobutyl, secondary butyl, tertiary butyl, n-amyl, isoamyl or n-hexyl. Preferred are lower alkyl groups of 1 to 3 carbon atoms as for example methyl, ethyl, n-propyl or isopropyl.

When R, $R_1$ or $R_2$ is a cycloalkyl group this may be a cycloalkyl group with 3 to 7 carbon atoms as for example a cyclopropyl, cyclobutyl, cyclopentyl, cyclohexyl or cycloheptyl group.

A lower alkyl group substituted by a cycloalkyl radical may be for example cyclopropyl-methyl, cyclopropyl-ethyl, cyclopropyl-n-propyl, cyclobutylmethyl, cyclobutyl-ethyl, cyclobutyl-n-propyl, cyclopentyl-methyl, cyclopentyl-ethyl, cyclopentyl-n-propyl, cyclohexylmethyl, cyclohexyl-ethyl, cyclohexyl-n-propyl, cycloheptylmethyl, cycoheptyl-ethyl or cycloheptyl-n-propyl.

The term aryl preferably comprises mononuclear groups such as phenyl, which may be substituted in one or more positions by substituents such as lower alkyl, hydroxy, lower alkoxy or halogen.

Moreover in addition to the meaning above when R and $R_1$ or the substituent of a lower alkyl group thereof is an aryl group, this aryl group comprises 6 to 10 carbon atoms and may be for example a mononuclear group e.g. a phenyl, tolyl, xylyl, ethylphenyl, propylphenyl, isopropylphenyl, butylphenyl, isobutylphenyl, sec.-butylphenyl, tert.-butylphenyl or naphthyl group.

If the substituents $R_1$ or $R_2$ can also represent together with the C(R)—N residue, or CH—N residue respectively, a heterocyclic radical, it is preferably a 5-membered nitrogen-containing ring such as pyrrolidine in proline and 4-hydroxy-pyrrolidine in hydroxy-proline, and pyroglutamic acid.

A heterocyclic residue as substituent of an optional substituted radical R, $R_1$ and $R_2$ may be a mono- or bicyclic, a monoaza or diazacyclic radical of aromatic character such as imidazolyl, as for example 4-imidazolyl, or indolyl, as for example 3-indolyl radical.

Moreover in addition when R or $R_1$ or the substituent of a lower alkyl group thereof is a heterocyclic ring containing one or more oxygen, nitrogen, or sulphur atoms this may be, for example, aziridine, oxetane, thiophene, furan, pyridine, azepine, isoxazole, thiazole, pyrimidine, diazepine, thiadiazol, triazol, triazine, or imidazole or indole as mentioned above.

When R or $R_1$ is a lower alkenyl group this may be a straight or branched chain alkenyl group with 2 to 6 carbon atoms, and may be, for example, an ethenyl, allyl, crotyl, methallyl, pentenyl or hexenyl group.

When R or $R_1$ represents a lower alkynyl group this may be straight or branched chain alkynyl group with 2 to 6 carbon atoms, and may be, for example, an ethynyl, propynyl, butynyl, pentynyl or hexynyl group.

When R and $R_1$ together form a polymethylene chain, comprising a residue of 2 to 7 carbon atoms, this may be for example $-(CH_2)_2-$, $-(CH_2)_3-$, $-(CH_2)_4-$, $-(CH_2)_5-$, $-(CH_2)_6-$, $-(CH_2)_7-$, $-(CH_2)_2CHCH_3(CH_2)_2-$ or $-(CH_2)_2NH(CH_2)_2-$.

The term etherified hydroxy is preferably lower alkoxy, such as methoxy, ethoxy, n-propyloxy, isopropyloxy or n-butyloxy and etherified mercapto is preferably lower alkylthio as for example methylthio, ethylthio, propylthio or isopropylthio.

The compounds containing S-substituted dithio groups are symmetrical or unsymmetrical residues of a compound of formula I bound to the other residue of a compound of formula I by a S-S-bridge, i.e.

A—S—S—B wherein A and B are the same or different and each is a residue of a compound of formula I formed by the loss of a hydrogen atom from a carbon atom in one of the substituents R, $R_1$ or $R_2$.

Examples of such compounds are those having the formulae Ia and Ib:

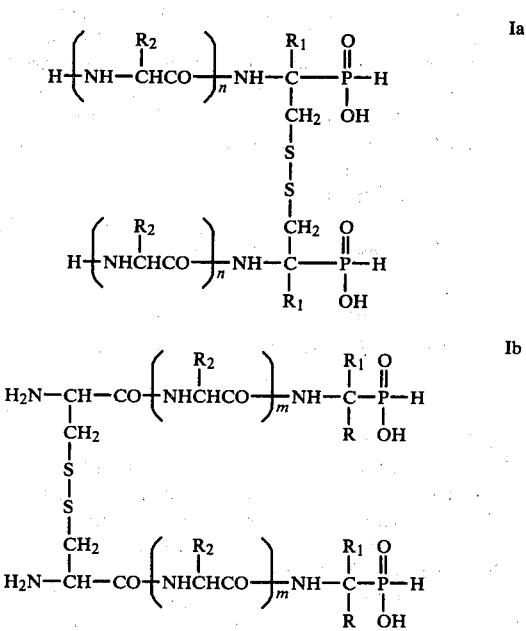

wherein

R, R₁ and R₂ have their previous significance and
n has its previous significance, and
m is 0, 1, 2 or 3.

Functionally modified carboxy is, e.g. esterified carboxy, especially lower alkoxycarbonyl, also phenyl-lower-alkoxycarbonyl or carbamoyl.

When R, R₁ or R₂ is a group substituted by —NR₃R₄, in which one or both the R₃ and R₄ groups are lower alkyl, these groups may be lower alkyl groups as defined above. The —NR₃R₄ group including the different meanings enumerated above may be for example, methylamino, dimethyl amino, methyl-ethylamino, ethylamino, diethylamino, propylamino, isopropylamino, dipropylamino or diisopropylamino.

The —NR₃R₄ groups in which R₃ and R₄ together form a polymethylene chain containing up to 6 carbon atoms which may optionally be interrupted by oxygen or nitrogen as for instance as substituent of R and R₁ and are preferably the morpholino or piperidino group.

Furthermore when R or R₁ is a group substituted by an aryloxy, the aryloxy group may be phenoxy, tolyloxy, xylyloxy, diiodo-hydroxy phenoxy.

The term halogen may be bromine or iodine but is preferably fluorine or chlorine.

Esters of the compounds of formula I are preferably the physiologically splittable esters of the compounds of formula I with low alkyl alcohols e.g. methanol, ethanol n-propanol and n-butanol, aralkyl alcohols e.g. benzyl alcohol and phenols, e.g. phenol. Other alcohols which may be used to form the corresponding ester of the compound of formula I are alkanoyloxymethanols e.g. acetoxymethanol or pivaloyloxymethanol; amino-lower-alkanoyloxymethanols e.g. α-amino-lower-alkanoyloxymethanols such as glycyloxymethanol, L-valyloxymethanol or L-leucyloxymethanol; and also 3-hydroxy-phthalide and 5-indanol.

Salts of the compounds of formula I and the physiologically splittable esters are preferably addition salts of the following therapeutically useful inorganic or organic acids or bases:

Examples of acids are hydrochloric, hydrobromic, sulphuric, phosphoric, methanesulphonic, ethanedisulphonic, acetic, trichloroacetic, oxalic, succinic, maleic, fumaric, malic, tartaric, citric and mandelic acids: examples of bases are lithium, sodium, potassium, calcium, magnesium, aluminium, iron, ammonium and substituted ammonium, hydroxides and carbonates, and heterocyclic bases.

Preferred starting materials of formula II and preferred end products of formula I are those wherein n=0 (the aminophosphonic acids themselves), n=1 (dipeptides); and n=2, 3 or 4 (oligopeptides). More preferred derivatives are α-aminophosphonic acids and dipeptides and especially preferred are 1-aminoethanephosphonic acid and dipeptides based on 1-aminoethane-phosphonic acid.

The starting materials of formula II are fully described, together with their production, in our copending British Applications Nos. 21000/76 and 48264/77.

The process of the present invention is conveniently carried out by contacting the reactants at a temperature between ambient and the boiling point of the reaction medium, preferably between ambient and 100° C. at atmospheric pressure. Water is preferably used as the sole reaction solvent although an aqueous organic solvent e.g. aqueous alcohol may be employed. The process is preferably carried out at normal pressure but superatmospheric pressures may be used if desired.

Depending upon the oxidising agent used, the process may be conducted with or without an excess of the oxidising agent or in the presence or absence of a catalyst, e.g. in the case of oxidations with $H_2O_2$, using $Fe^{3+}$ as catalyst.

A convenient mode of isolating the compound of formula I from the hydrohalide salt is to treat the reaction mixture with propylene oxide.

The peptide derivatives of formula I produced according to the process of the present invention have useful pharmaceutical properties which are fully described in U.S. Pat. No. 4,016,148 and Belgian Pat. Nos. 856724 and 856725. Thus the peptide derivatives potentiate the activity of antibiotics such as pencillin, cephalosporins and D-cycloserine. The peptide derivatives of formula I can be administered in combination with the antibiotic, or separately therefrom, if necessary by different routes. The ratio of peptide to antibiotic can vary widely depending on e.g. the peptide and antibiotic in question, the route of administration and the organism to be combatted.

The peptide derivatives of formula I also possess an antibacterial activity against gram positive and gram negative organisms such as *E.coli, P.vulgaris, Ps.aeuruginosa* and *S.aureus*. Thus, the peptide derivatives of formula I may be used as medicaments e.g. as pharmaceutical preparations containing them in association with a compatible pharmaceutical carrier material. The carrier may be any inorganic or organic inert carrier material suitable for enteral (e.g. oral) of parenteral administration, e.g. water, lactose, starch, magnesium stearate, gum arabic, gelatin, polyalkylene glycols and petroleum jelly. The pharmaceutical preparations can be made up in solid form (e.g. tablets, dragees, suppositories or capsules) or in liquid form (e.g. solutions, suspensions or emulsions). The pharmaceutical preparations may be sterilized and may contain adjuvants e.g. preservatives, stabilisers, wetting agents or salts for altering the osmotic pressure.

The peptide derivatives of formula I also possess plant growth regulant properties and herbicidal properties.

Moreover, the α-aminophosphonic acids produced according to the present process have, per se, useful plant growth regulating properties, which are fully described in U.S. Pat. No. 4,127,401.

Relative to the synthetic processes described for the compounds of formula I in U.S. Pat. No. 4,016,148, and in Belgian Pat. Nos. 856724 and 856725, the process of the present invention has the advantages of an easily accessible starting material and the achievement of optimal yields in the process of the invention.

The process of the present invention has the advantage that the final product has the same optical configuration as that of the starting material.

The following Examples further illustrate the present invention.

EXAMPLE 1

RS-1-Aminoethanephosphonous acid (0.018 M), mercuric chloride (0.036 M) and water (50 ml) were mixed and heated to reflux for 1 hour. The white insoluble mercurous chloride which formed was removed by filtration and the aqueous filtrate was evaporated to dryness. The oily residue was dissolved in ethanol (20 ml) and propylene oxide was added until precipitation was complete. Filtration gave RS-1-aminoethanephosphonic acid having m.p. 275°–277°. Mixed m.p. with authentic specimen 275°–277° (yield 100% of theory).

EXAMPLE 2

The method described in Example 1 was repeated using 1R-1-(L-alanylamino)-ethanephosphonous acid (0.034 M), mercuric chloride (0.068 M) and water (175 ml) to give 1R-1-(L-alanylamino)-ethanephosphonic acid which was recrystallised from ethanol/water m.p. 293°–5°, $[\alpha]_D^{20}$ −49.3° (1%, $H_2O$). Yield was 100% of theory.

EXAMPLE 3

The method described in Example 1 was repeated using 1S-1-(L-alanylamino)-ethanephosphonous acid (0.0048 M), mercuric chloride (0.0096 M) and water (25 ml) to give IS-1-(L-alanylamino)-ethanephosphonic acid which was recrystallised from ethanol/water, m.p. 290°–2° $[\alpha]_D^{20}$ +71.6° (1%, $H_2O$). Yield was 100% of theory.

EXAMPLE 4

The method described in Example 1 was repeated using 1R-1-(L-alanyl-L-alanyl-L-alanylamino)-ethanephosphonous acid (0.003 M), mercuric chloride (0.006 M) and water (25 ml) to give IR-1-(L-alanyl-L-alanyl-L-alanylamino)-ethanephosphonic acid m.p. 307°–8° decomp., $[\alpha]_D^{20}$ −100°(0.5% in 1 M NaOH). Yield was 100% of theory.

EXAMPLE 5

RS-1-Aminoethanephosphonous acid (0.05 M), cupric chloride (0.1 M) and water (20 ml) were mixed and warmed to 75° for 1 hour. The blue colour disappeared and the white cuprous chloride which formed was removed by filtration. The aqueous filtrate was evaporated to dryness and the oily residue was dissolved in ethanol (20 ml) and propylene oxide was added until precipitation was complete. Filtration gave RS-1-aminoethanephosphonic acid m.p. and mixed m.p. 275°–7°, identical to that obtained in Example 1. Yield was 100% of theory.

EXAMPLE 6

RS-1-Aminoethanephosphonous acid (0.05 M) and a saturated solution of bromine water (50 ml) was heated to 70° for 1 hour. The mixture was evaporated to dryness and the oily residue was successively treated with water and re-evaporated until a white solid was obtained. This solid was dissolved in ethanol (20 ml) and propylene oxide was added until precipitation was complete. Filtration gave RS-1-aminoethanephosphonic acid m.p. and mixed m.p. 275°–7°, identical to that obtained in Example 1. (Yield 100%).

EXAMPLE 7

RS-1-Aminoethanephosphonous acid (0.05 m) was dissolved in water (10 ML) and sulphur dioxide was passed through the mixture for 1 hour at 70°. The mixture was filtered and was evaporated to dryness to give a solid product. This solid was dissolved in ethanol saturated with dry hydrogen chloride, and the mixture evaporated to dryness. The residue was dissolved in ethanol (20 ml) and propylene oxide was added until precipitation was complete. Filtration gave RS-1-amino-ethanephosphonic acid m.p. and mixed m.p. 275°–7° identical to that obtained in Example (Yield 100%).

EXAMPLE 8

The method described in Example 5 was repeated using 1R-(L-alanylamino)-ethane-phosphonous acid (0.05 M), cupric chloride (0.1 M) and water (20 ml) to give 1R-1-(L-alanylamino)-ethanephosphonic acid identical to that obtained in Example 2.

EXAMPLE 9

The method described in Example 6 was repeated using 1R-1-(L-alanylamino)-ethane-phosphonous acid (0.05 M) and bromine water (50 ml) to give 1R-(L-alanylamino)-ethanephosphonic acid identical to that obtained in Example 2.

EXAMPLE 10

The method described in Example 7 was repeated using 1R-1-(L-alanylamino)-ethane-phosphonous acid (0.05 M) and sulphur dioxide to give 1R-1-(L-alanylamino)-ethanephosphonic acid identical to that obtained in Example 2.

EXAMPLE 11

A solution of 1R-1-(L-alanylamino)-ethanephosphonous acid (0.05 M) and 30% hydrogen peroxide were heated to 70° for 1 hour. The mixture was concentrated to about one ml. and formalin was added. The mixture was stirred at 50° for one hour until no peroxide could be detected. The mixture was evaporated to dryness and triturated with alcohol to give 1R-1-(L-alanylamino)-ethanephosphonic acid identical to that obtained in Example 2.

EXAMPLE 12

A mixture of 1R-1-(L-alanylamino)-ethanephosphonous acid (0.001 M) glucose oxidase Type II from Sigma Chem. Co. (1000 units), β-D-glucose (0.001 M), pH buffer to 5.3 (1.0 ml) was kept at 37°. A sample withdrawn after 30 minutes was found to contain 1R-1-(L-alanylamino)-ethanephosphonic acid by HPLC.

EXAMPLE 13

1-RS-1-(N-Benzyloxycarbonylamino)ethanephosphonous acid (0.1 M) and sodium bicarbonate (0.3 M) were dissolved in water (250 ml). Mercuric chloride (0.3 M) was added portionwise and the mixture was heated slowly up to 100° over 1 hour and maintained at this temperature for a further 1 hour. On cooling the resulting precipitate was filtered off and the filtrate acidified to pH 1–2. The precipitate which formed was extracted with ethyl acetate/petroleum ether to give 1RS-1-(N-benzyloxycarbonylamino)ethanephosphonic acid m.p. 110°–112°. Yield was 78% of theory. The benzyloxycarbonyl group may be removed by hydrogenolysis using palladium on charcoal to give RS-1-aminoethanephosphonic acid (identical to the product described in Example 1).

EXAMPLE 14

1-R-1-[(N-Benzyloxycarbonyl-L-alanyl)amino]ethanephosphonous acid (0.01 M) and sodium bicarbonate (0.03 M) were dissolved in water (25 ml). Mercuric chloride (0.03 M) was added and the mixture was stirred at room temperature for 1 hour. It was then heated to reflux for a further 1 hour. The mixture was then cooled, acidified with 2 N hydrochloric acid and extracted with ethyl acetate (3×100 ml).

The organic phase was dried (MgSO$_4$) and evaporated to give 1-R-1-[(N-benzyloxycarbonyl-L-alanyl)amino]ethanephosphonic acid having m.p. 171°–171.5°, $[\alpha]_D^{22}$ −30.5° (2%, C$_2$H$_5$OH). Yield was 58% of theory. The benzyloxycarbonyl group may be removed by hydrogenolysis using palladium on charcoal catalyst to give 1R-1-(L-alanylamino)-ethanephosphonic acid (identical to the product described in Example 2).

EXAMPLE 15

The method described in Example 15 was repeated using 1-RS-1-[(N-benzyloxycarbonyl-L-alanyl)amino]ethanephosphonous acid (0.01 M) to give 1-RS-1-[(N-benzyloxycarbonyl-L-alanyl)amino]ethanephosphonic acid having m.p. 148°–150°, $[\alpha]_D^{22}$ −27.4° (2%, C$_2$H$_5$OH). Yield was 42% of theory. The benzyloxycarbonyl group may be removed by hydrogenolysis using palladium on charcoal catalyst to give 1RS-1-(L-alanylamino)-ethanephosphonic acid.

What we claim is:

1. A process for the production of an α-aminophosphonic acid or a peptide derivative thereof of formula:

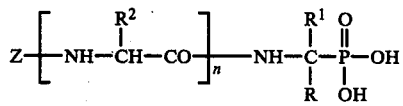  I wherein

R and R$_1$ may be the same or different and each can be hydrogen, deuterium or an optionally substituted lower alkyl group, lower alkenyl, lower alkynyl, cycloalkyl, aryl or heterocyclic radical containing one or more oxygen, nitrogen or sulphur atoms and which may be fused to an aromatic ring, a lower alkyl group substituted by a cycloalkyl radical, a lower alkyl group substituted by an aryl radical, a lower alkyl group substituted by a heterocyclic radical as defined above or R and R$_1$ together form a polymethylene chain optionally interrupted by an oxygen, nitrogen or sulphur atom, or R$_1$ represents, together with the C(R)—N< residue to which it is attached, the atoms required to complete a heterocyclic radical; and R$_2$ can be hydrogen, optionally substituted lower alkyl, cycloalkyl, aryl or lower alkyl substituted by a cycloalkyl radical, lower alkyl substituted by a heterocyclic radical containing one or more nitrogen atoms; by a heterocyclic radical containing one or more nitrogen atoms, or R$_2$ together with the C(H)—N residue to which it is attached, may represent the atoms required to complete a heterocyclic radical; and n is 0, 1, 2, 3 or 4; comprising oxidising, using an oxidising agent, a compound having the formula:

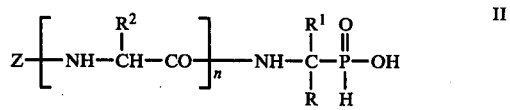  II wherein

R, R$^1$, R$^2$ and n have their previous significance, and

Z is H or a protecting group usually used for an amino group.

2. A process as claimed in claim 1 wherein the oxidising agent is a salt of a metal (capable of existing in higher and lower valency states) in its higher valency state in the presence of a hydroxylic solvent; an oxide of a metal or non-metal capable of releasing oxygen; an oxyacid (or a salt thereof) of a metal or non-metal, capable of releasing oxygen; an organic compound capable of releasing oxygen; a halogen or halo-organic compound in the presence of water; a direct source of oxygen; or a peroxide.

3. A process as claimed in claim 2 wherein the oxidising agent is cupric chloride or mercuric chloride.

4. A process as claimed in claim 2 wherein the oxidising agent is sulphur dioxide.

5. A process as claimed in claim 2 wherein the oxidising agent is bromine water.

6. A process as claimed in claim 2 wherein the oxidising agent is hydrogen peroxide.

7. A process as claimed in claim 1 wherein, in compounds of formula I and II, n is zero.

8. A process as claimed in claim 1 wherein, in the compounds of formula I and II, n is 1.

9. A process as claimed in claim 1 wherein, in the compounds of formula I and II, n is 2, 3 or 4.

10. A process as claimed in claim 1 wherein the compounds of formula I are α-aminophosphonic acids and dipeptide derivatives.

11. A process as claimed in claim 10 wherein the compound of formula I is 1-aminoethanephosphonic acid and peptide derivatives based on this acid.

12. A process according to claim 1, wherein Z is H.

* * * * *